United States Patent [19]

Bartz et al.

[11] Patent Number: 4,699,516

[45] Date of Patent: Oct. 13, 1987

[54] APPARATUS AND METHODS FOR DETERMINING CELL SIZE

[75] Inventors: Arnold M. Bartz, Granville; Stanley H. Wineland, Thornville, both of Ohio

[73] Assignee: The Dow Chemical Company, Midland, Mich.

[21] Appl. No.: 666,151

[22] Filed: Oct. 29, 1984

[51] Int. Cl.⁴ ..................... G01N 21/55; G01N 21/43
[52] U.S. Cl. ................................... 356/445; 356/136
[58] Field of Search ............... 356/71, 445, 448, 128, 356/335, 136, 447

[56] References Cited

U.S. PATENT DOCUMENTS

| | | | |
|---|---|---|---|
| 2,050,486 | 8/1936 | Davis et al. | 356/136 |
| 3,174,414 | 3/1965 | Myer | 356/71 |
| 3,953,739 | 4/1976 | Colombo et al. | 250/571 |
| 3,975,711 | 8/1976 | McMahon | 356/71 |
| 4,329,052 | 5/1982 | Colombo et al. | 356/335 |
| 4,412,961 | 11/1983 | DiBiasi et al. | 356/448 |

FOREIGN PATENT DOCUMENTS

| | | | |
|---|---|---|---|
| 2504199 | 8/1976 | Fed. Rep. of Germany | 356/445 |
| 1178258 | 1/1970 | United Kingdom . | |
| 1195197 | 6/1970 | United Kingdom . | |
| 1210260 | 10/1970 | United Kingdom . | |

*Primary Examiner*—R. A. Rosenberger

[57] ABSTRACT

The surface of a cellular body which is flat except for a number of cavities is examined by placing a transparent light refracting medium against the surface and transmitting light through the medium toward its interface with the body surface at such an angle of incidence to the interface that light incident on the interface at the body surface is refracted into the body and light incident on the interface at the cavities is totally reflected internally of the medium and then outwardly thereof. The reflected light produces an image having readily distinguishable zones of lightness and darkness indicative of the cavities and body material, respectively. The image is displayed in such manner as to enable either of the relatively dark and light zones to be counted. An optical coupling liquid is interposed between the body surface and the refracting medium to compensate for small gaps or irregularities in the body surface.

25 Claims, 6 Drawing Figures

|  | | Prism Material | | |
|---|---|---|---|---|
|  | | ZnS | Sapphire | Glass |
| $n_p$ | | 2.42 | 1.76 | 1.53 |
| $\theta_{min} = \sin^{-1}(1/n_p)$ | | 24.4° | 34.6° | 40.8° |
| $\theta_{cpo} = \sin^{-1}(n_o/n_p)$ | $n_o = 1.3$<br>$n_o = 1.5$<br>$n_o = 3$ | 32.5°<br>38.0°<br>-- | 47.6°<br>58.4°<br>-- | 58.2°<br>78.6°<br>-- |
| $\theta_{cps} = \sin^{-1}(n_s/n_p)$ | $n_s = 1.3$<br>$n_s = 1.6$<br>$n_s = 3$ | 32.5°<br>41.4°<br>-- | 47.6°<br>65.4°<br>-- | 58.2°<br>--<br>-- |
| $\theta_i$ optimum $= \theta_v$ | | 30° | 45° | 50° |
| $\theta_{coa} = \sin^{-1}(1/n_o)$ | $n_o = 1.3$<br>$n_o = 1.5$<br>$n_o = 3$ | 50.3°<br>41.8°<br>19.4° | 50.3°<br>41.8°<br>19.4° | 50.3°<br>41.8°<br>19.4° |
| $\theta_o = \sin^{-1}(\frac{n_p}{n_o} \sin\theta_i)$ | $n_o = 1.3$<br>$n_o = 1.5$<br>$n_o = 3$ | 68.6°<br>53.8°<br>23.8° | 73.2°<br>56.1°<br>24.5° | 64.4°<br>51.4°<br>23.0° |

TABLE I
FIG. 5

| $n_o$ \ $n_s$ | 1.3 | 1.6 | 3 |
|---|---|---|---|
| 1.3 | 90° | - | - |
| 1.5 | 60° | - | - |
| 3.0 | 25.7° | 32.2° | 90° |

$\theta_{cos} = \sin^{-1}(n_s/n_o)$

TABLE II
FIG. 6

APPARATUS AND METHODS FOR DETERMINING CELL SIZE

This invention relates to apparatus and methods for facilitating the examination of a body surface that is substantially flat except for the presence of cavities. The invention is particularly useful in the determination of the size of cells in a body of cellular material.

BACKGROUND OF THE INVENTION

In the manufacture of cellular products from foamed polymers the size of the cells has significant effects on many of the physical properties of such products. For example, thermal insulating and compressive strength properties are directly related to cell size. To establish manufacturing procedures for the production of cellular products having the desired physical characteristics, therefore, it is important to be able to determine accurately the size of cells resulting from various production techniques. Once the cell size resulting from one production technique has been established, the technique may be maintained or varied, as required, to produce a cellular product corresponding to predetermined specifications. To ensure that the appropriate technique is being maintained, it is desirable to be able to monitor the production by making rapid examinations of samples of the product at frequent intervals during its production run.

The importance of cell size to the physical properties of a particular product is well known and at least two proposals have been made heretofore for determining cell size. Each proposal involves cutting a thin section from a foam sample and then, according to one proposal, transmitting light through a predetermined area of the sample to produce an image and then projecting the image for visual inspection. In the second proposal a predetermined area of the surface of a thin sample is illuminated, and light reflected by such surface of the sample is transmitted to a microscope for visual examination.

Both proposals rely on the ability of a viewer to distinguish the contrast between the intensities of the light transmitted through or reflected by the sample at the walls of the cells and at the exposed cavities created by cutting of the sample. In many instances the intensities of the transmitted or reflected light are too nearly equal to enable the observer to discriminate accurately between the cell walls and the cell cavities, thereby resulting in significant errors in determining cell size. Theoretically, the problem in distinguishing between cells and cell walls may be overcome by forming a sample having a thickness corresponding substantially to the diameter of a single cell. In practice, however, it is not possible to form such samples consistently. As a consequence cell walls or struts internal of the sample cannot be distinguished from those walls or struts at the surface of the sample. The inability of an observer to distinguish between cell walls at and below the surface of a sample is particularly pronounced in those instances in which the sample is formed of material which is transparent. Thus, it is virtually impossible to obtain accurate cell size determination using currently available methods.

A distinct disadvantage resulting from the slicing of a thin section sample from a body of foam material is that the slicing equipment presently available invariably causes the formation of irregularities in the exposed surfaces of the cell walls, thereby preventing the preparation of a truly representative sample. For example, many polymers are so fragile that the slicing operation results in the tearing away of sections of a wall and the formation of ragged edges. Particularly is this true in those instances in which the sample has a thickness approaching that of only one cell diameter.

A further disadvantage of the known methods of examining samples of the kind referred to is that the inspection requires too great a time to complete. Thus, if an inspection reveals deficiencies in a product, it is possible that a substantial quantity of the deficient product will have been produced during the time it takes to complete the inspection and before corrective adjustments can be made in the production process.

Apparatus and methods according to the invention overcome the disadvantages referred to above and are applicable not only to the examination of opaque, translucent, and transparent cellular products, but to other objects as well.

SUMMARY OF THE INVENTION

The examination of a cellular body according to the invention for determining the size of the cells involves the cutting of the body at one side thereof along a plane to form a sample. This will cause the walls of those cells in the plane of the cut to be severed so that the remaining portions of such walls are substantially coplanar and terminate in the plane of the cut. Between the adjacent wall portions are gaps or cavities of varying widths, depths, and shapes, depending upon the size and particular portion of a cell traversed by the cutting tool.

A transparent prism having polished, planar faces is applied to the sample so that a selected face of the prism confronts and bears upon those portions of the cell walls which lie in the plane of the cut. The force with which the prism bears on the sample is sufficiently light as to avoid significant compressive deformation of the sample. The area of the prism face is sufficient to span a number of the cavities formed by severing of the cells. The exposed surfaces of the cavities are spaced from the confronting face of the prism and in a direction inward of the sample. The space between the cavity and the overlying prism face is occupied by air or other environmental gas.

The prism is illuminated by a beam of preferably white light that is directed toward the prism/sample interface at an angle of incidence which is at least as great as the critical angle of the environmental gas, but less than the critical angle of the sample. As a consequence, those portions of the beam incident on the prism/sample interface at the cell walls are refracted into the sample, whereas those portions of the beam incident on the prism/sample interface at the cell cavities are totally reflected internally along a path leading outwardly of the prism. The reflected light forms an image wherein the cavities appear as relatively light zones and the cell walls appear as relatively dark zones. The contrast between the light and dark zones is substantial. The image may be magnified, if desired, and projected onto a screen or displayed on a video monitor, for example, thereby easily enabling the number of severed cell walls at the surface of the sample to be counted. Once the number of cell walls in a predetermined distance is known, the cell size may be calculated.

To compensate for the inevitable irregularities in the cell walls caused by cutting of a fragile sample, a thin coating of transparent liquid is interposed between the sample and that face of the prism which confronts the sample. The liquid fills the irregularities and forms an optical coupling between the severed cell walls of the sample and the prism.

THE DRAWINGS

Apparatus adapted for use in practicing the invention is illustrated in the accompanying drawings wherein:

FIG. 5 is a table of data calculated for several different kinds of prism materials; and FIG. 6 is another table showing critical angles at a liquid/sample interface of a range of refractive indices.

DETAILED DESCRIPTION

Figure 1:
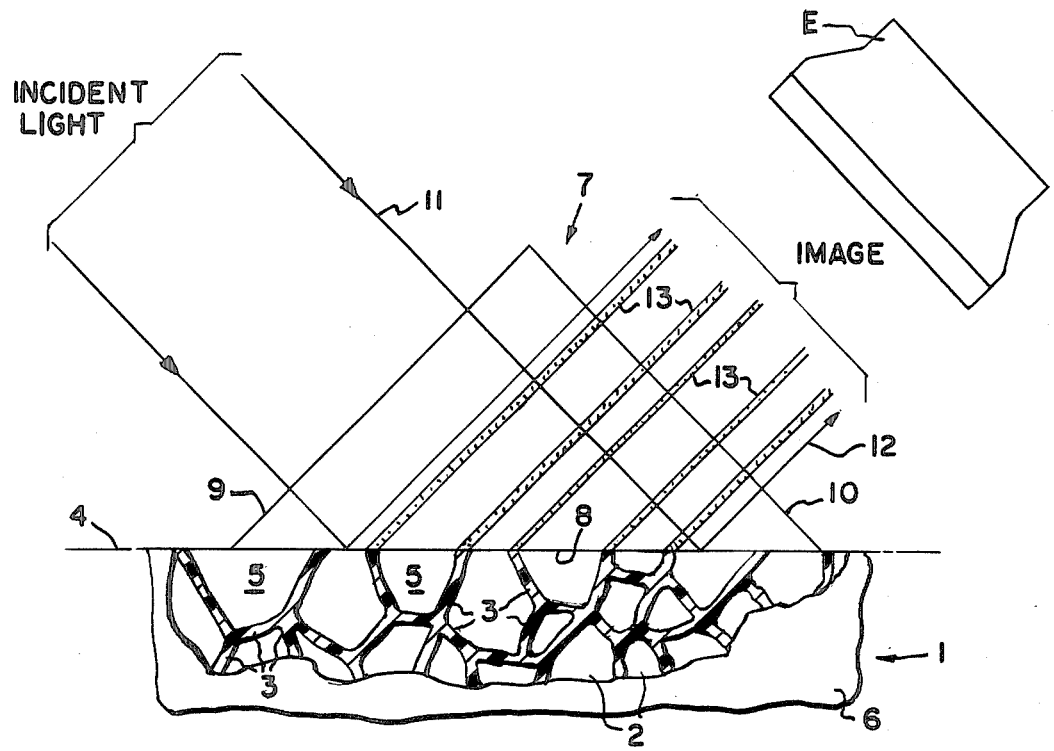
FIG. 1 is a diagrammatic view, partly in elevation and partly in section, of elementary apparatus illustrative of the invention.

Apparatus and methods according to the invention are especially adapted for use in the examination of a cellular body 1, shown in FIG. 1, to measure the size of the cells. The body is resiliently compressible or deformable and is formed of polymeric material that may be opaque, translucent, or transparent. The body may or may not have an outer skin. In any case, the body 1 has a plurality of cells 2 defined and spaced by walls 3.

Preparatory to the examination, the body 1 is cut in a known manner along one side thereof to form a plane 4 in which all of the edges of the severed cell walls 3 lie. Those portions of the cells 2 between adjacent severed wall portions form cavities or gaps 5 exposed to air or other environmental gas. Cutting of the body along the plane 4, therefore, results in the forming of a sample 6 having a substantially flat or planar surface interrupted by a plurality of cavities of different widths and depths. The width and depth of a cavity depend upon not only the diameter of the cell, but also upon that part of the cell through which the cut was made. The thickness of the sample is immaterial, but it should be such as to be convenient to handle.

The apparatus illustrated in FIG. 1 includes a light refractive medium such as a transparent prism 7 having at least three planar faces, one of which is adapted to confront the cut surface of the sample and bear sufficiently lightly upon the severed wall portions 3 of the cells 2 as to avoid significant deformation of the walls. The area of the prism face chosen to confront the sample should be sufficiently large as to span a number of cavities 5 representative of the cellular structure of the body.

The method according to the invention relies upon the optical phenomenon of total internal reflection which occurs when light passing through a first medium of relatively high refractive index impinges on the interface between the first medium and a second medium of relatively low refractive index and at an angle of incidence greater than the critical angle of the second medium.

For proper performance of the method according to the invention the prism 7 should be formed of transparent material having an index of refraction so related to the refractive indices of the environmental gas and the material from which the body 1 is made that light incident on the prism/sample interface at a cell wall 3 will be substantially wholly refracted into the sample, whereas light incident on the prism/sample interface at a cavity 5 will be totally internally reflected away from the sample.

The refractive indices are known for air, other gases, and each of a large number of materials from which prisms and cellular bodies may be formed, and the refractive indices of other materials may be computed according to Snell's law. Materials suitable for use as prisms include zinc sulfide, zinc selenide, and sapphire, but other materials, including glass and quartz, also may be used. The refractive index of air and other gases is 1, the refractive index of glass is 1.53, of zinc selenide is 2.3, of zinc sulfide is 2.4, and of sapphire is 1.76. The refractive index of polystyrene, one polymer from which the body 1 may be formed, is 1.6 The refractive indices of other polymers and prism materials may be obtained from existing tables or computed.

Once the refractive indices of the prism 7 and the body 1 are known, the prism may be shaped so that incident light perpendicular to one of its shorter faces will impinge upon the face forming the hypoteneus at an angle having a value between the prism's critical angles relative to the polymer and relative to air. For example, the critical angle of zinc selenide relative to polystyrene is 44° and relative to air is 26°. The configuration of a zinc selenide prism for use with a cellular polystyrene sample, therefore, should be so chosen that its smaller angle is between 26° and 44°. An obtuse prism having a smaller angle of 30° thus will be appropriate and easy to manufacture. Prisms having other angles may be used, however, depending on the relationship referred to above with respect to critical angles. For example, if a sapphire prism is to be used in the examination of a polystrene body, it is convenient to use a right angular prism whose smaller angles are 45°. Any prism used may be truncated to conserve space.

The prism 7 shown in FIG. 1 is a right angular prism having angles of 45°, 90°, and 45°. The prism has three planar, polished faces 8, 9, and 10 and is so oriented to the sample 6 that the face 8 confronts and bears lightly upon the coplanar, severed ends of the cell walls 3. The face 8 is of such area as to span a number of the cavities 5.

In the arrangement shown in FIG. 1 a beam 11 of preferably white light is directed upon and perpendicular to the prism face 9. The beam passes through the prism toward that face 8 which interfaces the prism and the sample 6. The refractive index of the prism is such that the angle of incidence of the beam on the face 8 is less than the critical angle of the material forming the body 1, but greater than the critical angle of air. Thus, those portions of the beam 11 incident on the face 8 overlying the cavities 5 are totally reflected internally and thence along a path extending outwardly of the prism through the third face 10. The reflected portions of the beam are indicated by the reference character 12. Those portions of the beam 11 incident on the face 8 overlying a cell wall 3 will be refracted into the sample. Thus, the reflected beam 12 will be interrupted by laterally spaced apart, relatively dark zones indicated by the reference character 13.

Since some portions of the light incident on the prism face 8 are totally reflected and other portions are refracted into the sample, the reflected light from the interface between the prism and the sample will form an image having relatively light and dark zones in which the lighter zones represent the cavities and the darker zones represent the severed walls between adjacent cavities. Interposed in the path of the reflected light is an ocular device E or other suitable collector by means of which the image may be viewed directly or projected in a conventional manner onto a movie or other conventional screen (not shown).

In the image the severed cell walls at the prism/sample interface will appear as dark zones, whereas the cavities between the cell walls will appear as much lighter zones, regardless of whether the body under observation is opaque, translucent, or wholly transparent. Thus, the contrast between the cavities and the cell walls is substantial, thereby clearly delineating the cavities and the cell walls at the prism/sample interface, but none of the cell walls which lie inwardly of the sample's surface will appear in the image. It is fairly easy, therefore, to count either the cells or the cell walls of the projected image. Once the number of cell walls has been counted, the cell diameter D can be computed using the equation $D = 1.62 \, L/N$ wherein N represents the number of cell walls counted in a straight line distance L.

Figure 2:
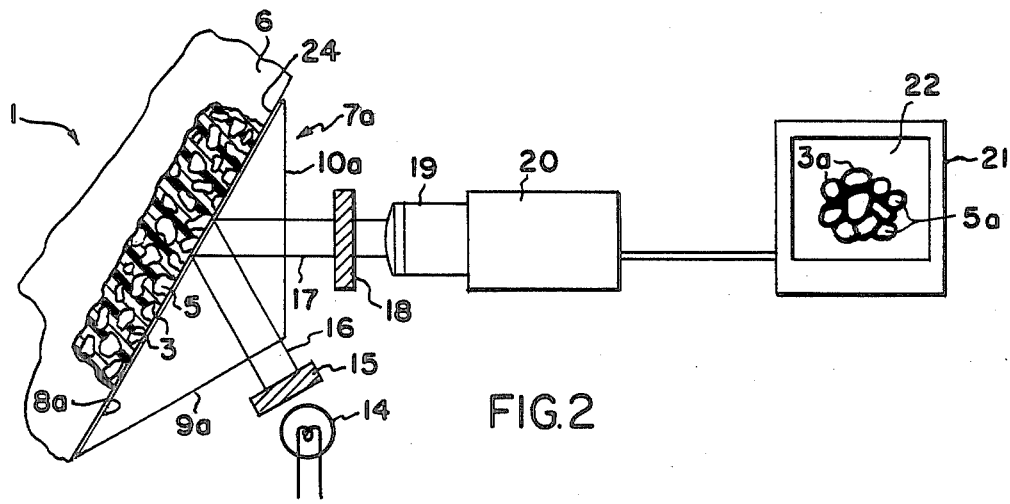
FIG. 2 is a largely diagrammatic view illustrating apparatus suitable for use in practicing the invention on a commercial scale.

FIG. 2 illustrates apparatus useful in the commercial scale practice of the method. The body 1 and the sample 6 are the same as described earlier, but the light refracting medium is an obtuse prism 7a. The additional apparatus includes suitable means (not shown) for supporting the prism, a quartz-halogen bulb or other suitable, preferably white light source 14, and a diffuser 15 through which a beam 16 of the light is directed perpendicularly onto the prism face 9a in the same manner described earlier. The diffuser prevents a concentration of light directly opposite the light source.

Light incident on the prism/sample interface at the cell walls 3 is refracted into the sample, whereas light incident on the prism/sample interface at the cavities 5 is totally internally reflected along a path which extends outwardly through the prism face 10a as a beam 17 similar to the beam 12 described earlier. If a sapphire or other birefringent material is used for the prism, the reflected beam 17 should be passed through a polarizer 18 and thence collected and magnified by a microscope objective 19 and transmitted to a video camera 20. From the camera the image produced by the reflected light is transmitted to a display unit such as a video monitor 21 having a screen 22 on which the image may be displayed. The displayed image will show the cell wall portions 3 at the prism/sample interface as black or dark zones 3a and the cavities 5 as white or light zones 5a, thereby providing substantial contrast between the cell walls and cavities. If desired, the prism face 8a may be provided with a reticle scale which also is displayed on the screen 22, thereby facilitating counting of the number of cell walls in a selected distance.

It is not essential that white light be used as the incident light. Light of a selected color may be used in some instances. White light is preferred, however, because it enhances the contrast between cavities and the cell walls when the image is displayed on movie and video screens.

Figure 3:
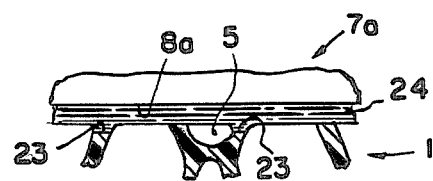
FIG. 3 is a fragmentary, greatly enlarged detail of a portion of the structure shown in FIG. 1.

The foregoing explanation of the apparatus shown in FIGS. 1 and 2 assumes that the severed edges of the cell walls are perfectly flat and coplanar. In actual practice it is not presently possible to produce such edges because commercially available cutting devices are incapable of cutting the fragile cell-defining walls of a polymer without the formation of small irregularities or gaps in the exposed surfaces of the cut walls. Typical gaps are shown at 23 in FIG. 3. Such gaps will cause some portions of the surfaces of the walls 3 to lie below the plane 4 at the prism/sample interface, thereby enabling air to interface the prism at the gaps and causing light incident on the prism/sample interface at the gaps to be totally reflected. These gaps thus will appear in the displayed image as light or white portions in the dark zones representing the cell walls and could be misinterpreted as constituting small cellular cavities in the walls. Such gaps could be compensated for to some extent by urging the prism against the sample under sufficient force to deform the cut walls so that the entire surface of each wall will engage the prism. Such deformation, however, could collapse one or more of the cut walls and cause the prism face to bear against the base of one or more cavities, thereby causing the displayed image to indicate falsely the absence of such cavities.

In the preferred embodiment of the invention the presence of small irregularities in the severed walls of the cells is compensated for by interposing between the prism and the sample an optical coupling comprising a thin coating 24 of a transparent liquid such as paraffin oil, kerosene, or silicone oil ranging in viscosity from 200 to 10,000 cp. Other liquids may be used, however, as is explained hereinafter.

The presence of an optical coupling liquid between the prism and the sample fills the gaps 23 in the cell walls caused by the cutting of the body 1 to form the sample and provides an optical path which permits light incident on the prism/sample interface at such gaps to pass into the sample, rather than undergoing total internal reflection. The coupling liquid, therefore, reconstitutes the cell walls so that they act optically as if they had been cut perfectly. Thus, the use of the coupling liquid enables an imperfectly cut wall to appear in the displayed image as a continuous surface without having to apply excessive compressive force on the sample.

When an optical coupling liquid is used two conditions must be satisfied if the projected image is to display accurately the cavity/cell wall relationship of the sample under examination. First, there must be total internal reflection (TIR) at the interface between the liquid and the air in a cavity and, second, there must not be TIR at the interface between the liquid and a wall 3. The necessary relationships to ensure satisfaction of these two conditions are explained hereinafter with reference to FIG. 4 wherein the reference characters therein denote the following:

R = A ray of white light $\theta_i$ = Angle of incidence for the light ray within the prism approaching the prism/liquid interface. This angle also is the vertex angle of the prism for normal external incidence.

$\theta_o$ = Angle of refracted ray in the coupling liquid coating. This angle is also equal to the angle of incidence at the liquid/sample interface and the angle of reflection at the liquid/air interface.

$\theta_s$ = Angle of refracted ray in the sample.

$\theta_a$ = Angle of refracted ray in air.

$\theta_{cpo}$ = Critical angle for the prism/liquid interface.

$\theta_{cpa}$ = Critical angle for the prism/air interface.

$\theta_{cos}$ = Critical angle for the liquid/sample interface.

$\theta_{coa}$ = Critical angle for the liquid/air interface.

$\theta_v$ = Vertex angle of the prism.

$n_p$ = Refractive index of the prism material.

$n_o$ = Refractive index of the coupling liquid.
$n_s$ = Refractive index of the sample.

Figure 4:
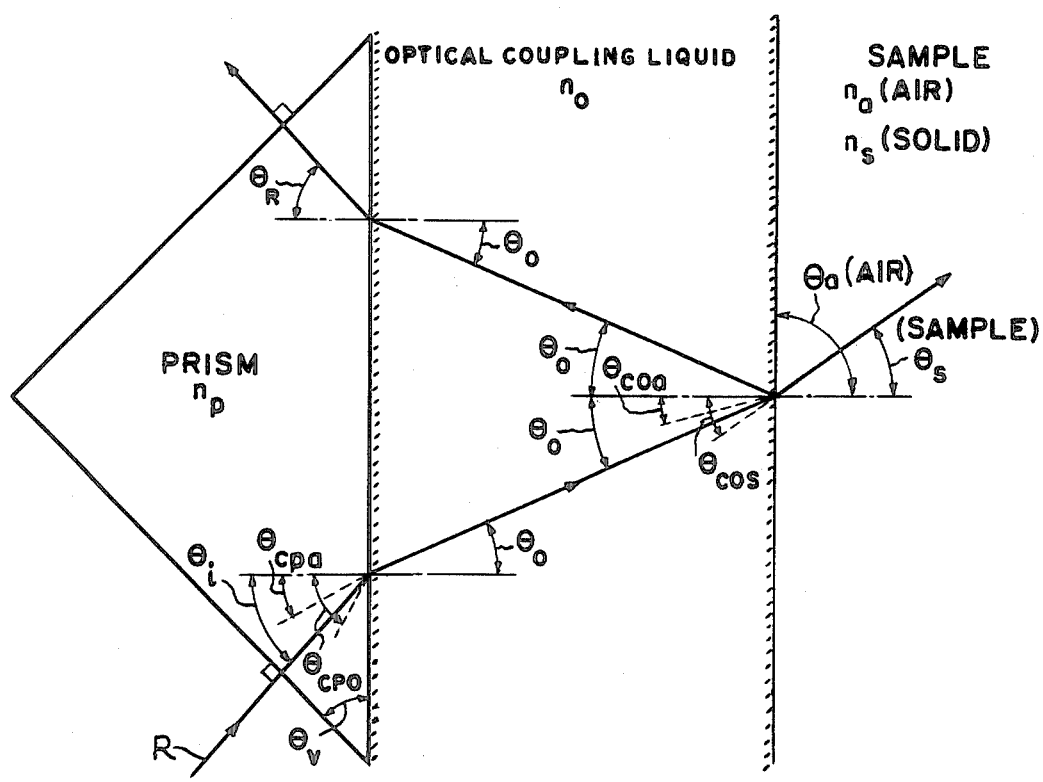
FIG. 4 is an enlarged diagrammatic view illustrating the criteria to be considered when practicing the invention.

The incident light ray R shown in FIG. 4 is perpendicular to one of the two shorter faces of the prism and impinges on the prism/liquid interface at an angle of incidence $\theta_i$ which is less than the critical angle $\theta_{cpo}$ of the coupling liquid. The ray R thus is refracted into the liquid at the angle $\theta_o$ and proceeds toward and impinges upon the liquid/sample interface at an angle of incidence which is less than the critical angle $\theta_{cos}$ of the body material, but greater than the critical angle $\theta_{coa}$ of air. Thus, if the liquid/sample interface at the ray R is formed by a section of a cell wall, the ray will be refracted into the body at the angle $\theta_s$. However, if the liquid sample interface at the ray R is formed by air in a cavity, the ray will be totally reflected at the angle $\theta_o$ and redirected through the liquid to the prism. The reflected ray is refracted by the prism at the angle $\theta_R$ and directed outwardly thereof through its second shorter face.

The criteria necessary to produce the desired results of TIR at a liquid/cavity interface and no TIR at a liquid/sample interface best may be explained by the following applications of Snell's law.

Since the refractive index of air is 1.0, the application of Snell's law to the light ray R in FIG. 4 results in the following equation:

$$n_p \sin\theta_i = n_o \sin\theta_o = n_s \sin\theta_s = \sin\theta_a \qquad \text{(Equation 1)}$$

For the light ray R at a liquid/air interface to be subjected to TIR, angle $\theta_a$ must equal or exceed 90°. Thus, $\sin\theta_a \geq 1$. When equation 1 is rewritten to include this requirement the result is:

$$n_p \sin\theta_i = n_o \sin\theta \geq 1 \qquad \text{(Equation 2)}$$

which indicates that the minimum possible values for $\theta_o$ in the coupling liquid and $\theta_i$ in the prism are:

$$\theta_o \min = \sin^{-1}(1/n_o) = \theta_{coa} \qquad \text{(Equation 3)}$$
and
$$\theta_i \min = \sin^{-1}(1/n_p) = \theta_{cpa} \qquad \text{(Equation 4)}$$

Note that equations 3 and 4 correspond to two of the critical angles shown in FIG. 4.

For the light ray R at a liquid/sample interface to be refracted into the sample, thereby satisfying the condition that the ray not be subjected to TIR at such interface, the angle of refraction $\theta_s$ must be less than 90° or stated differently, $\sin\theta_s \leq 1$. When equation 1 is rewritten to include this requirement the result is:

$$n_p \sin\theta_i = n_o \sin\theta \leq n_s \qquad \text{(Equation 5)}$$

Thus, $\theta_o$ is restricted to the value $$\theta_o \leq \sin^{-1}(n_s/n_o) \qquad \text{(Equation 6)}$$

and $\theta_i$ is restricted to the value $$\theta_i < \sin^{-1}(n_s/n_p) \text{ (Equation 7)}$$

The maximum value of the incident angle $\theta_i$ given by equation 7 is subject to the condition that no TIR take place at the interface between the prism and the liquid. This requires the angle of refraction $\theta_o$ in the liquid to be less than 90° with the result that $\sin\theta_o < 1$. Rewriting equation 1 to reflect this requirement yields a second restriction on the angle of incidence:

$$\theta_i \leq \sin^{-1}(n_o/n_p) \qquad \text{(Equation 8)}$$

Thus, the angle of incidence for the light at the prism/liquid interface must lie between the extremes given in equations 4, 7, and 8:

$$\sin^{-1}(1/n_p) < \theta_i < \sin^{-1}(n/n_p) \qquad \text{(Equation 9)}$$

where the maximum allowable value for the angle of incidence $\theta_i$ is:

$$\theta_i \max = \sin^{-1}(n/n_p) \qquad \text{(Equation 10)}$$

n being the smaller of $n_o$ and $n_s$.

The vertex angle $\theta_v$ of the prism must be chosen to give a value to $\theta_i$ which satisfies the boundary conditions represented by equation 9. For light incident normal to the prism face, the vertex angle is just equal to $\theta_i$, so that $\theta_v$ can be substituted for $\theta_i$ in equation 9. The incident angle $\theta_i$ is determined primarily by the available prism geometry options. It is clear from equation 9 that, for a given sample index of refraction and prism geometry, the prism material itself is not limited to a specific value of refractive index. This means that it is possible to select the prism material on the basis of characteristics other than the refractive index only. A compilation of some actual values for the angles shown in FIG. 4 is presented in the Tables of FIGS. 5 and 6 for a range of prism, coupling liquid, and sample refractive indices.

One important non-optical characteristic of the prism material to be considered in the construction of apparatus for practicing the method is abrasion resistance. As samples are repeatedly interfaced with the prism and adjusted slightly to obtain a uniform liquid coupling between the prism face and the sample, considerable scratching of the prism face can occur if the prism is formed of a soft material such as zinc sulfide. It is preferred, therefore, to use a prism formed of a harder material. Sapphire, because of its extreme hardness and relatively high refractive index, is an excellent material to use for the prism.

Equations 4, 7, and 8 indicate that the choice of $\theta_i$ becomes severely limited as the refractive index $n_o$ of the liquid coupling approaches the refractive index of air, i.e., 1. Since most liquids have refractive indices at least 30% greater than that of air, the liquid index $n_o$ has little practical effect on the choice of $\theta_i$ (and thus on the prism geometry) for a particular application. Consequently, the coupling liquid can be chosen on the basis of its wetting characteristics, chemical inertness to the sample material, low volatility, and the like, rather than its refractive index. For example, the refractive index $n_o$ of the coupling liquid can be either greater or lesser than that of the sample and still enable the method to be performed. This is because the light rays refracted at the liquid/sample interface into the sample enter the latter at the same angle as would be the case if no liquid were present. This can be demonstrated from equation 1 by rewriting it as:

$$\sin\theta_s = (n_o/n_s)\sin\theta_o = (n_o/n_s)[(n_p/n_o)\sin\theta_i] \qquad \text{(Equation 11)}$$

Equation 11 can be rearranged to:

$$\sin\theta_s = (n_p/n_s)\sin\theta_i \qquad \text{(Equation 12)}$$

which is Snell's Law for the case in which there is no optical coupling liquid.

Similar results are obtained for the ray R that is totally reflected from the liquid/air interface. Defining $\theta_R$ as the angle of the reflected ray entering the prism from the liquid layer, and applying Snell's law:

$$n_o \sin\theta_o = n_p \sin\theta_R \qquad \text{(Equation 13)}$$

which is equivalent to:

$$\sin\theta_R = (n_o/n_p)(n_p/n_o)\sin\theta_i \qquad \text{(Equation 14)}$$

and which, upon simplifying, becomes:

$$\theta_R = \theta_i \qquad \text{(Equation 15)}$$

Again, this result corresponds to that which would be obtained if no optical coupling liquid were interposed between the prism and the sample. Thus, the only function of the coupling liquid is to displace the air in the small gaps or irregularities produced by cutting of the cell walls and thereby enable the light to be refracted into the sample. The result is an image which conforms to the appearance that the cell wall would exhibit if the cut were perfect.

A sapphire prism having a vertex angle of 45° will have light incident at the liquid/air interface at an angle $\theta_o$ that is greater than the critical angle for that interface for all liquids having refractive indices ranging from 1.3 to more than 3. However, the angle $\theta_{coa}$ is less than the critical angle $\theta_{cos}$ for samples having indices ranging from 1.3 to 3, as can be seen from the values in Tables I and II. Thus, the sapphire prism will produce the desired image for a wide range of combinations of sample and liquid refractive indices, even in those cases in which the refractive index of the sample is less than that of the coupling liquid.

The optical coupling liquid may be brushed, sprayed, or otherwise applied to the sample or to that face of the prism which confronts the sample. In either event the thickness of the liquid coating should be insufficient to fill the cavities 5.

A distinct advantage of the invention over the prior cell counting techniques referred to earlier is that, when using the method according to the invention, it is not necessary to cut a thin sample from the body under examination. It is only necessary to ensure that the body is cut along one side thereof to provide a substantially planar surface against which one face of the prism may bear. Thus, a body need be cut only once to form a sample, and the sample may be of such size that it conveniently may be held and manipulated by hand. These characteristics, coupled with the ease of distinguishing between cell walls and cavities, enable the preparation and examination of a sample to be completed considerably more quickly than has been possible heretofore. Thus, the need for modification in a process for the production of a cellular product can be detected and corrective action taken with less delay than formerly has been the case.

Although the foregoing description has been concerned primarily with the examination of cellular bodies formed of foamed polymers, the applicability of the method and apparatus according to the invention is by no means so limited. The apparatus and method are adaptable to the examination of hairline fractures, woven fabrics, and other objects of the kind wherein the interface between any such object and a light refracting medium comprises a substantially planar surface interrupted by one or more cavities.

What is claimed is:

1. Apparatus for use in determining the size of cells in a body composed of cellular material, said apparatus comprising a transparent, light refracting medium having a flat face; a body of cellular material having a critical angle of incidence, said body being cut along a plane at one side thereof to form a surface having a plurality of externally open cavities containing a gas and being spaced from one another by intervening portions of said body material terminating at said plane in substantially coplanar free edges, said body and said face confronting one another with said face and said free edges forming a substantially coplanar interface without appreciable deformation of said free edges and with said face spanning a selected area of said surface containing a plurality of said cavities; means for directing light into and through said medium toward said interface at an angle of incidence to said interface that is less than the critical angle of incidence of said body material and greater than the critical angle of incidence of said gas, whereby light incident on said interface at said free edges of said body material passes wholly into said body and light incident on said interface at said cavities is totally reflected internally of said medium along a path leading outwardly of said medium to produce an image having relatively light and dark zones indicative of said cavities and said free edges, respectively; means in said path for collecting said reflected light; and means for displaying said image.

2. Apparatus according to claim 1 wherein said medium is a prism.

3. Apparatus according to claim 1 including a coating of transparent liquid between said face of said medium and said free edges and forming an optical coupling therebetween.

4. Apparatus according to claim 3 wherein said coating has a thickness less than the depth of said cavities.

5. Apparatus according to claim 3 wherein said liquid comprises an oil.

6. Apparatus according to claim 5 wherein said oil has a viscosity of between about 200 and 10,000 cp.

7. Apparatus according to claim 3 wherein said coating is applied to said face of said medium.

8. Apparatus according to claim 3 wherein said coating has a thickness less than the depth of said cavities.

9. Apparatus according to claim 1 wherein said medium is a prism formed of a material selected from the class composed of zinc selenide, zinc sulfide, sapphire, quartz and glass.

10. Apparatus according to claim 1 including means for diffusing the light directed onto said medium.

11. Apparatus according to claim 1 including means for polarizing the reflected light.

12. Apparatus according to claim 1 wherein said light is white.

13. Apparatus according to claim 1 wherein the material forming said body is opaque.

14. Apparatus according to claim 1 wherein the material forming said body is transparent.

15. Apparatus according to claim 1 wherein the material forming said body is translucent.

16. A method of determining cell size in a body composed of cellular material having a critical angle of incidence, said method comprising cutting said body at one side thereof along a plane to produce an exposed surface having therein a plurality of externally open cavities containing a gas and beign spaced from one another by intervening portions of said body material having substantially coplanar free edges in said plane; establishing without appreciable deformation of said free edges an interface between the free edges of a selected area of said surface spanning a plurality of said cavities and a flat face of a transparent, light refracting medium; directing light through said medium at an angle of incidence to said interface that is less than the critical angle of incidence of said body material and greater than the critical angle of incidence of said gas, whereby light incident on said interface at said free edges is refracted wholly into said body and light incident on said interface at said cavities is totally reflected internally of said medium along a path leading outwardly thereof to form an image having relatively darker and lighter zones indicative of said intervening portions and said cavities, respectively; and displaying said image.

17. The method according to claim 16 including counting the number of darker zones in a selected length of said image.

18. The method according to claim 16 including magnifying said image prior to displaying it.

19. The method according to claim 16 including interposing between said surface of said body and said flat face of said medium a coating of transparent liquid.

20. The method according to claim 19 wherein said coating has a thickness less than the depth of said cavities.

21. The method according to claim 19 wherein said coating is applied to said face of said medium.

22. The method according to claim 19 wherein said coating comprises an oil.

23. The method according to claim 22 wherein said oil has a viscosity of between about 200 and 10,000 c.p.

24. The method according to claim 19 wherein said coating is applied to said free edges of said body.

25. The method according to claim 16 wherein said light is white.

* * * * *

UNITED STATES PATENT AND TRADEMARK OFFICE
CERTIFICATE OF CORRECTION

PATENT NO. : 4,699,516

DATED : October 13, 1987

INVENTOR(S) : Arnold M. Bartz and Stanley H. Wineland

It is certified that error appears in the above-identified patent and that said Letters Patent is hereby corrected as shown below:

Column 7, line 62, change "$\theta_i < \sin^{-1}(n_s/n_p)$ (Equation 7)" to -- $\theta_i \leq \sin^{-1}(n_s/n_p)$ (Equation 7) --; line 68, change "$\sin\theta_o < 1$" to -- $\sin\theta_o \leq 1$ --.

Column 8, line 57, change "no" to -- $n_o$ --.

Column 11, line 3, change "beign" to -- being --.

Signed and Sealed this

First Day of March, 1988

Attest:

DONALD J. QUIGG

Attesting Officer

Commissioner of Patents and Trademarks